(12) United States Patent
Riman et al.

(10) Patent No.: US 8,951,540 B2
(45) Date of Patent: *Feb. 10, 2015

(54) BIOMIMETIC HYDROXYAPATITE SYNTHESIS

(75) Inventors: Richard E. Riman, Belle Mead, NJ (US); Christina Sever, Old Bridge, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/619,087

(22) Filed: Sep. 14, 2012

(65) Prior Publication Data

US 2013/0022653 A1    Jan. 24, 2013

Related U.S. Application Data

(63) Continuation of application No. 11/622,927, filed on Jan. 12, 2007, now Pat. No. 8,287,914.

(60) Provisional application No. 60/758,207, filed on Jan. 12, 2006.

(51) Int. Cl.
| | | |
|---|---|---|
| *A61K 9/00* | (2006.01) | |
| *B82Y 5/00* | (2011.01) | |
| *A61K 33/42* | (2006.01) | |
| *A61L 27/46* | (2006.01) | |

(52) U.S. Cl.
CPC .............. *A61K 33/42* (2013.01); *A61L 27/46* (2013.01); *A61L 2430/02* (2013.01); *Y10S 977/773* (2013.01); *Y10S 977/904* (2013.01)
USPC ............................ 424/400; 977/773; 977/904

(58) Field of Classification Search
None
See application file for complete search history.

(56) References Cited

U.S. PATENT DOCUMENTS

| | | |
|---|---|---|
| 5,783,217 A | 7/1998 | Lee et al. |
| 6,013,591 A | 1/2000 | Ying et al. |
| 6,387,414 B1 | 5/2002 | Akashi et al. |
| 6,887,488 B2 | 5/2005 | Cui et al. |
| 2005/0186249 A1 | 8/2005 | Riman et al. |

FOREIGN PATENT DOCUMENTS

| | | | | |
|---|---|---|---|---|
| WO | WO2007/009477 | * | 1/2007 | .............. A61L 27/46 |
| WO | WO2007/084858 | | 7/2007 | |

OTHER PUBLICATIONS

Suchanek et al. In Biomaterials, 25, 4647-4657, 2004.*
Morissette et al. in Drug Delivery Reviews, 56 (2004) 275-300.*
Wang et al. in Materials Chemistry and Physics 95, 145-149 (2006).*
Hutchens S.A. et al., "Biomimetic synthesis of calcium-deficient hydroxyapatite in a natural hydrogel", Biomaterials, vol. 27, No. 26, Sep. 1, 2006, pp. 4661-4670.
Morissette et al., High-throughput crystallization: polymorphs, salts, co-crystals and solvates of pharmaceutical solids, Advanced Drug Delivery Reviews, vol. 56, pp. 275-300 (2004).

* cited by examiner

*Primary Examiner* — Dennis Heyer
(74) *Attorney, Agent, or Firm* — Fox Rothschild LLP

(57) ABSTRACT

A method for preparing nanoscale hydroxyapatite particles by combining an amount of a calcium ion source, which includes calcium acetate, and an amount of a phosphate ion source, wherein the amounts are sufficient to produce nanoscale hydroxyapatite particles and the amounts are combined under ambient conditions to produce the hydroxyapatite particles. Nanoscale hydroxyapatite particles are also presented.

10 Claims, 13 Drawing Sheets

BIOMIMETIC HYDROXYAPATITE SYNTHESIS

CROSS REFERENCE TO RELATED APPLICATIONS

This application is a Continuation of U.S. patent application Ser. No. 11/622,927, which was filed on Jan. 12, 2007, which claims priority to U.S. Provisional Application Ser. No. 60/758,207, which was filed on Jan. 12, 2006. The foregoing applications are hereby incorporated by reference in their entireties.

STATEMENT REGARDING FEDERALLY SPONSORED RESEARCH

The U.S. Government has a paid-up license in this invention and the right in limited circumstances to require the patent owner to license others on reasonable terms as provided for by the terms of grant DGE033196 awarded by the National Science Foundation.

BACKGROUND OF THE INVENTION

Hydroxyapatite (HAp, chemical formula $Ca_{10}(PO_4)_6(OH)_2$) has attracted the attention of researchers over the past thirty years as an implant material because of its excellent biocompatibility and bioactivity. HAp has been extensively used in medicine for implant fabrication. It is commonly the material of choice for the fabrication of dense and porous bioceramics. Its general uses include biocompatible phase-reinforcement in composites, coatings on metal implants and granular fill for direct incorporation into human tissue. It has also been extensively investigated for non-medical applications such as a packing material/support for column chromatography, gas sensors and catalysts, as a host material for lasers, and as a plant growth substrate.

Previously explored methods of hydroxyapatite synthesis for particles include plasma spraying, hydrothermal synthesis, freeze drying, sol-gel, phase transformation, mechanochemical synthesis, chemical precipitation, and precipitation in simulated body fluid (SBF). All of these methods produce products with varying levels of purity, size, crystallinity, and yield. Plasma spraying, hydrothermal synthesis, sol-gel, phase transformation, mechanochemical synthesis, and chemical precipitation require elevated temperatures and/or extreme pH values in the fabrication of hydroxyapatite. These conditions can raise important questions among biologists when considering the material for in vivo applications because they are not biomimetic and, in most cases, do not yield biomimetic structures or morphologies. Furthermore, precipitation in simulated body fluid has such a low yield or long reaction time, it is not practical for use in manufacturing implants.

Therefore, a need exists for hydroxyapatite synthesis to take place at room temperature and optional neutral pH to allow the exploration of synthesis with live cells, including those in living organisms.

SUMMARY OF THE INVENTION

There is provided, in accordance with the present invention, a method for preparing nanoscale hydroxyapatite particles by combining an amount of a calcium ion source, which includes calcium acetate, and an amount of a phosphate ion source, wherein the amounts are sufficient to produce nanoscale hydroxyapatite particles and the amounts are combined under essentially ambient conditions to produce the hydroxyapatite particles.

One embodiment includes a stable colloidal suspension of nanoscale hydroxyapatite particles suspended in a biocompatible ionic solution prepared by the method of the present invention, wherein the ionic solution includes physiological concentrations of phosphate and acetate anions and sodium or potassium cations.

Also provided are powdered hydroxyapatite particles having a BET surface area between about 200 and about 3000 $m^2/g$ and a particle size between about 1 nm and about 9 nm.

In one embodiment, a stable colloidal suspension of the hydroxyapatite particles suspended in a biocompatible ionic solution is provided.

Also provided is a kit for use in preparing nanoscale hydroxyapatite particles, wherein the kit includes (a) an amount of a calcium ion source, which includes calcium acetate, and (b) an amount of a phosphate ion source, wherein the amounts are sufficient to produce nanoscale hydroxyapatite particles when combined under ambient conditions.

DETAILED DESCRIPTION OF THE INVENTION

Figure 1A:
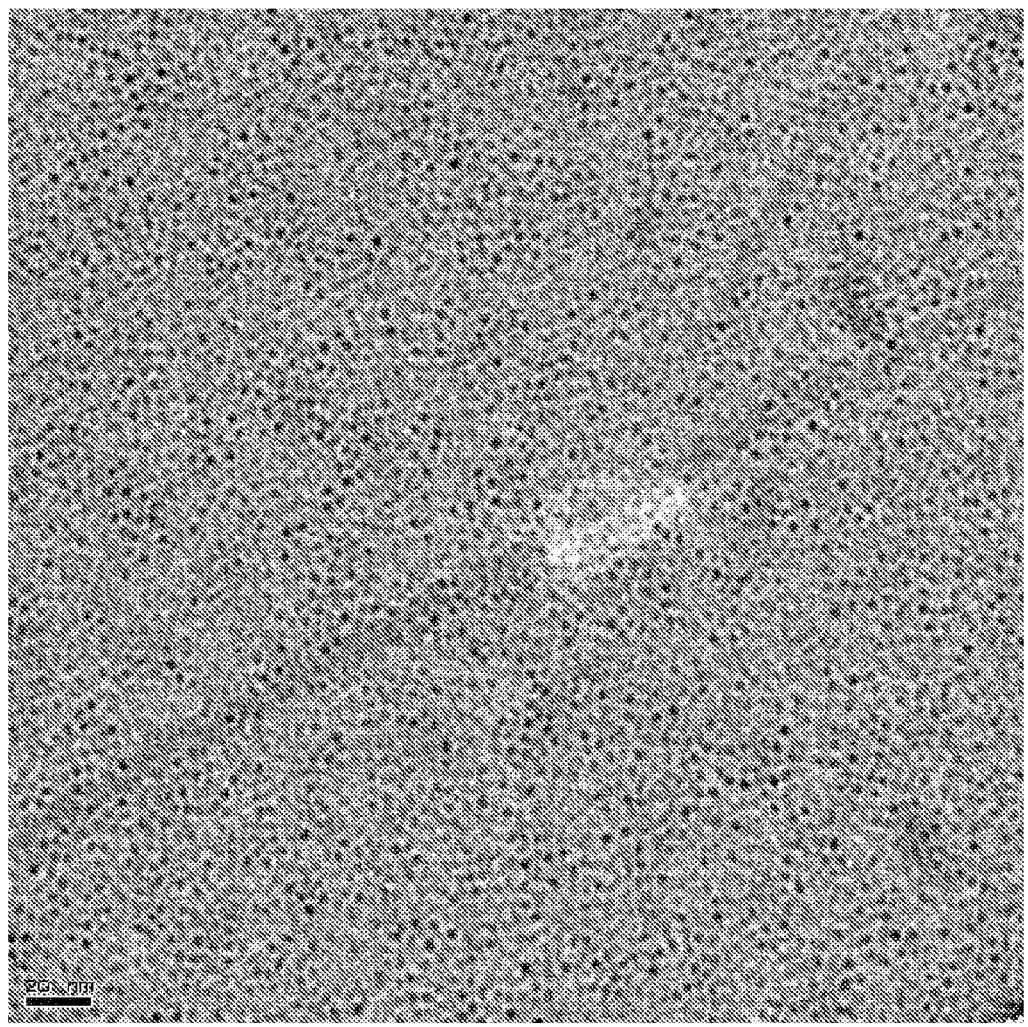
FIGS. 1a-d are transmission electron microscopy (TEM) images of particles prepared according to the method of Example 2.
Figure 1B:
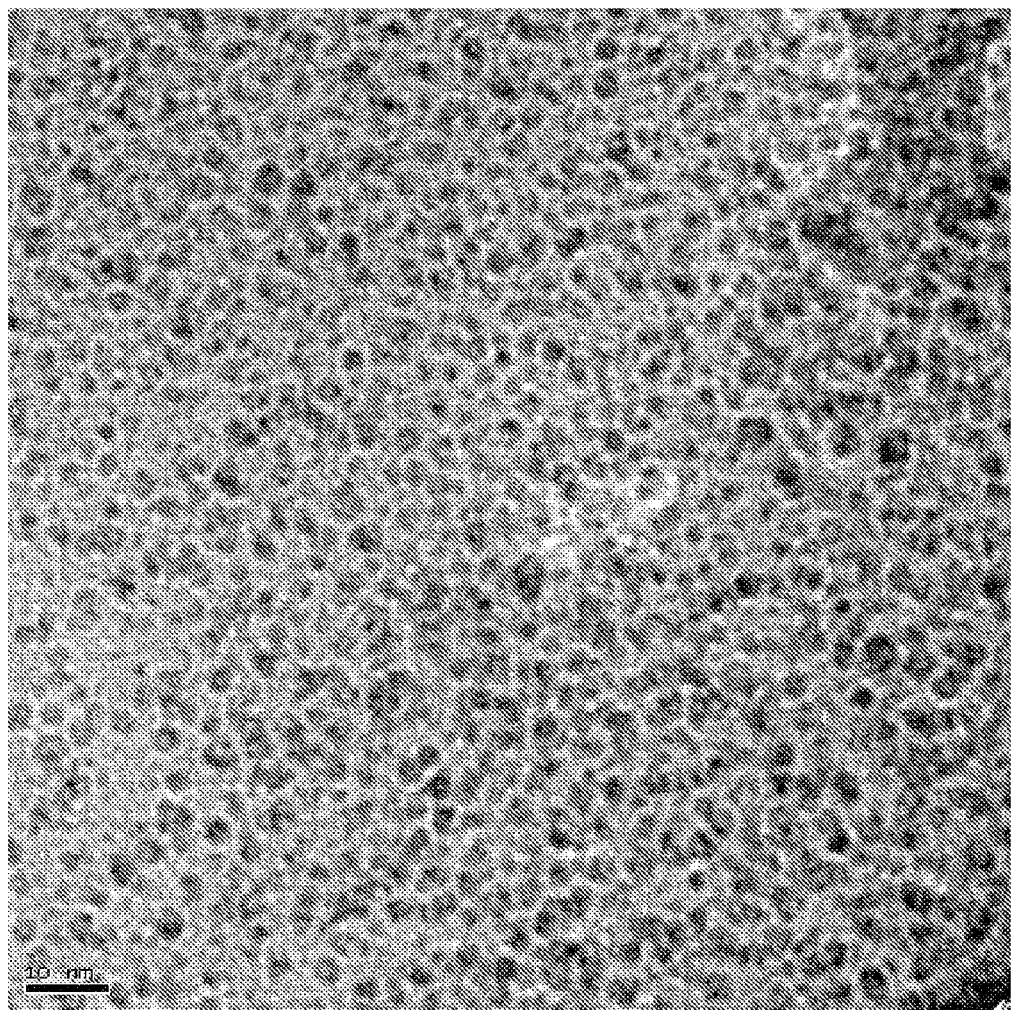
Figure 1C:
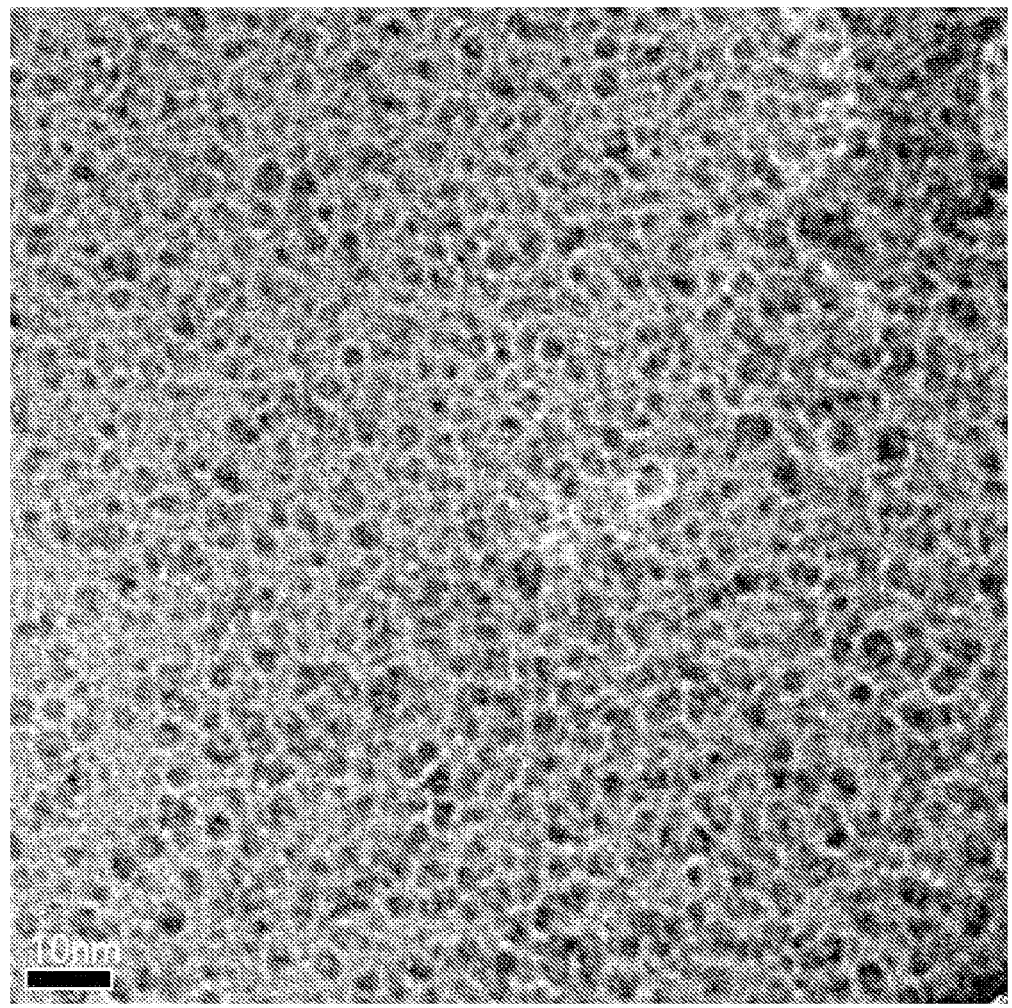
Figure 1D:
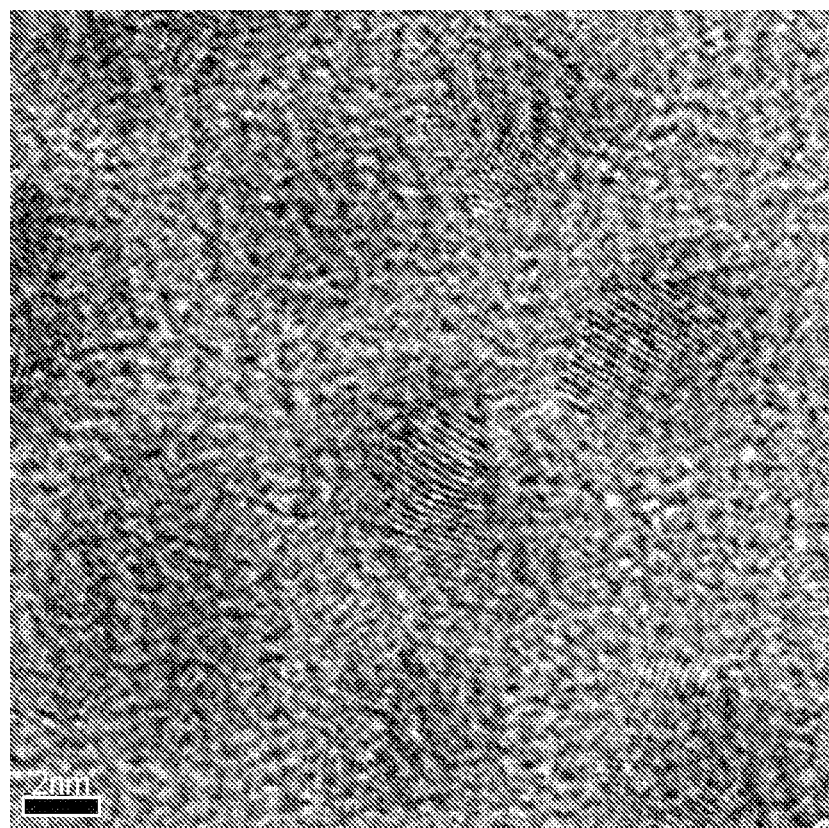
Figure 2A:
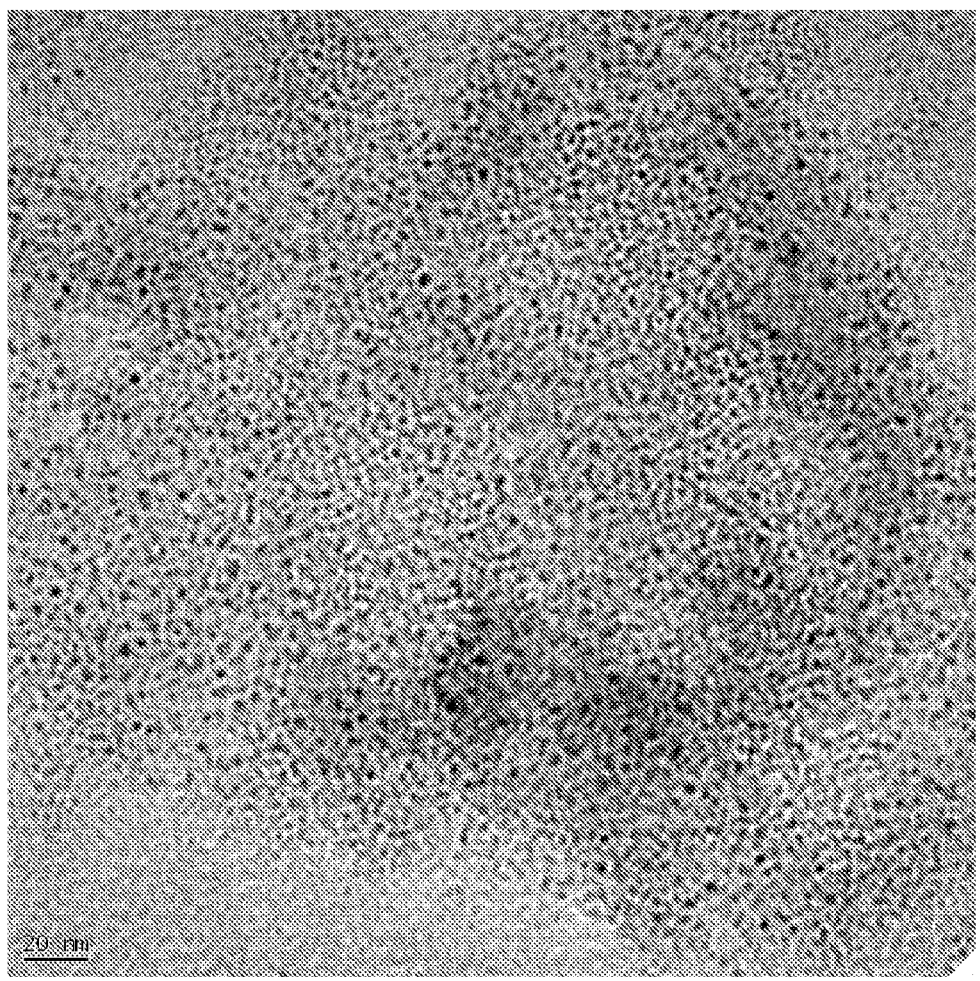
FIGS. 2a-b are TEM images of particles prepared according to the method of Example 3.
Figure 2B:
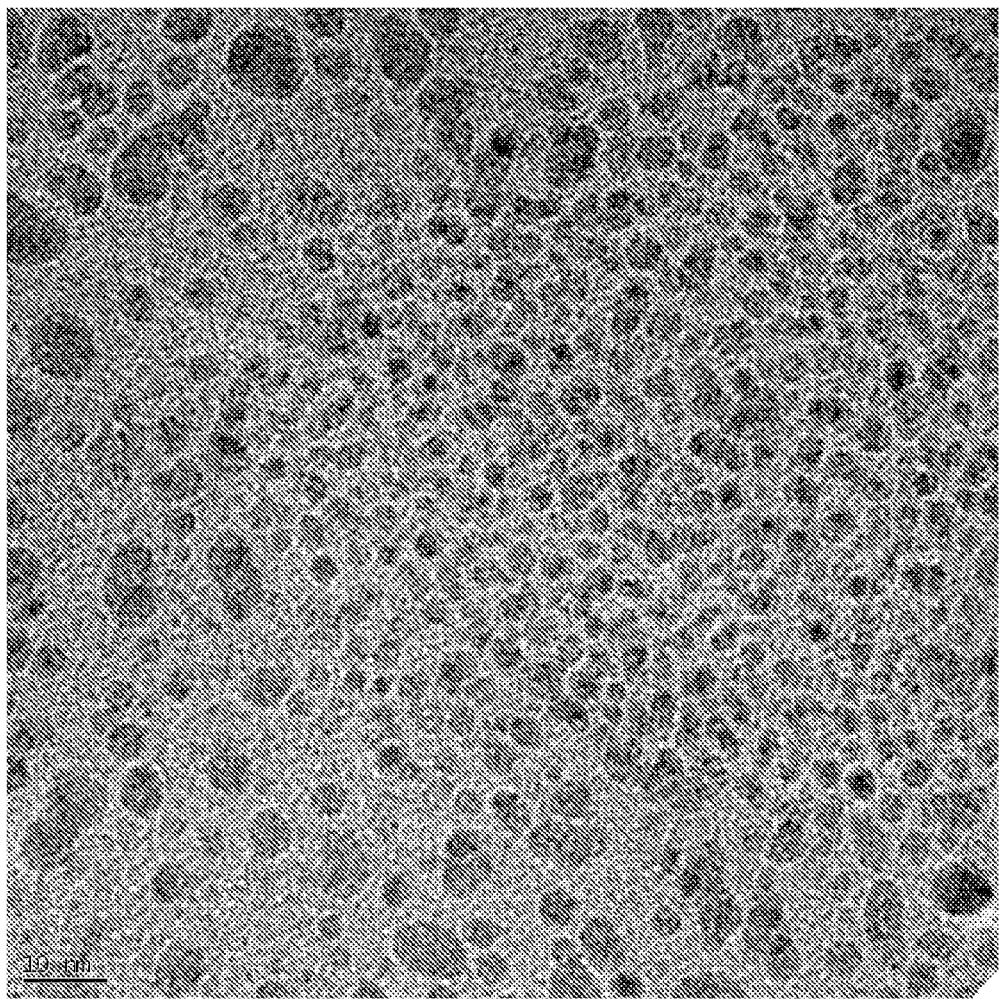
Figure 2C:
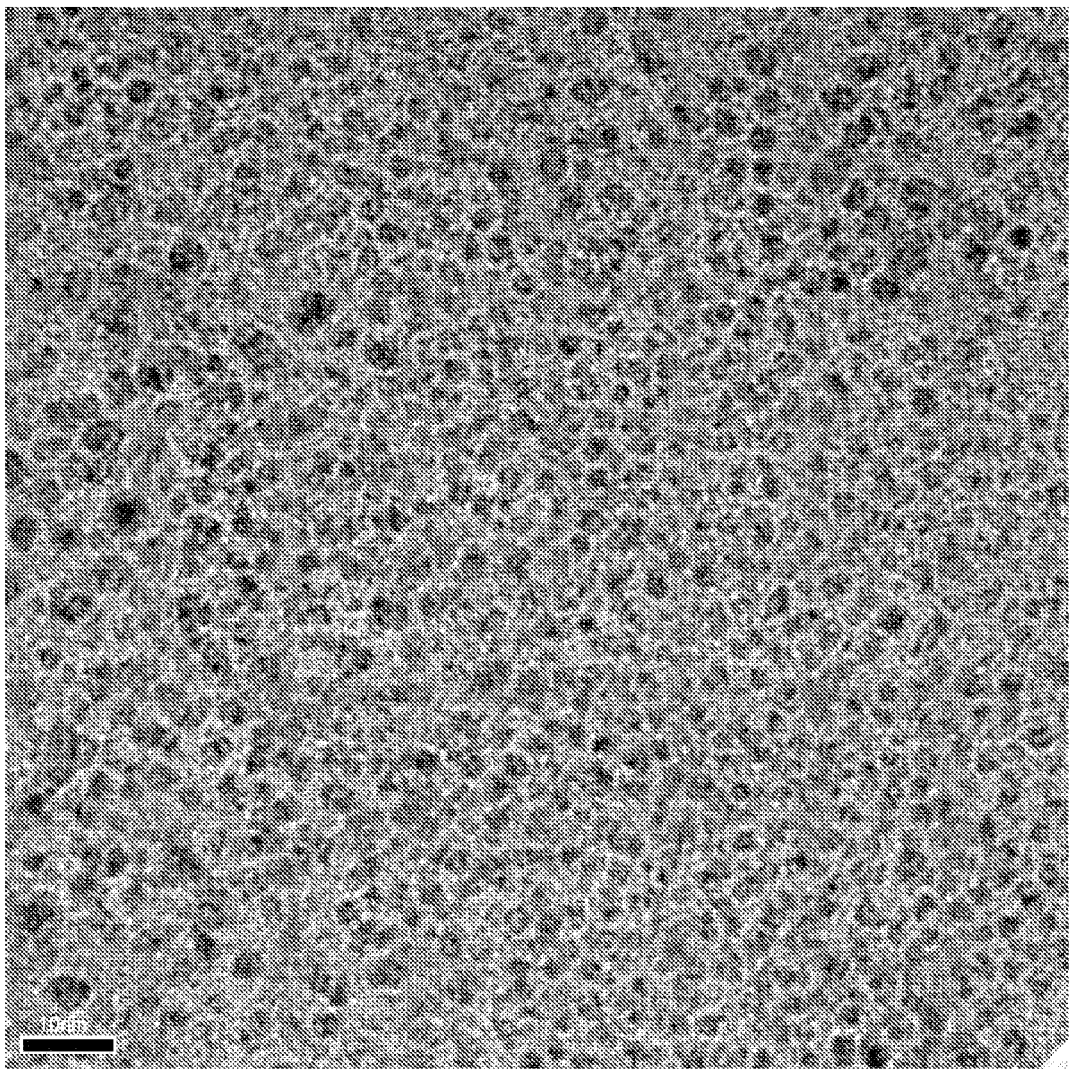
FIG. 2c is a TEM image of particles prepared according to the method of Example 3 at a higher magnification than the images of FIGS. 2a-b.
Figure 2D:
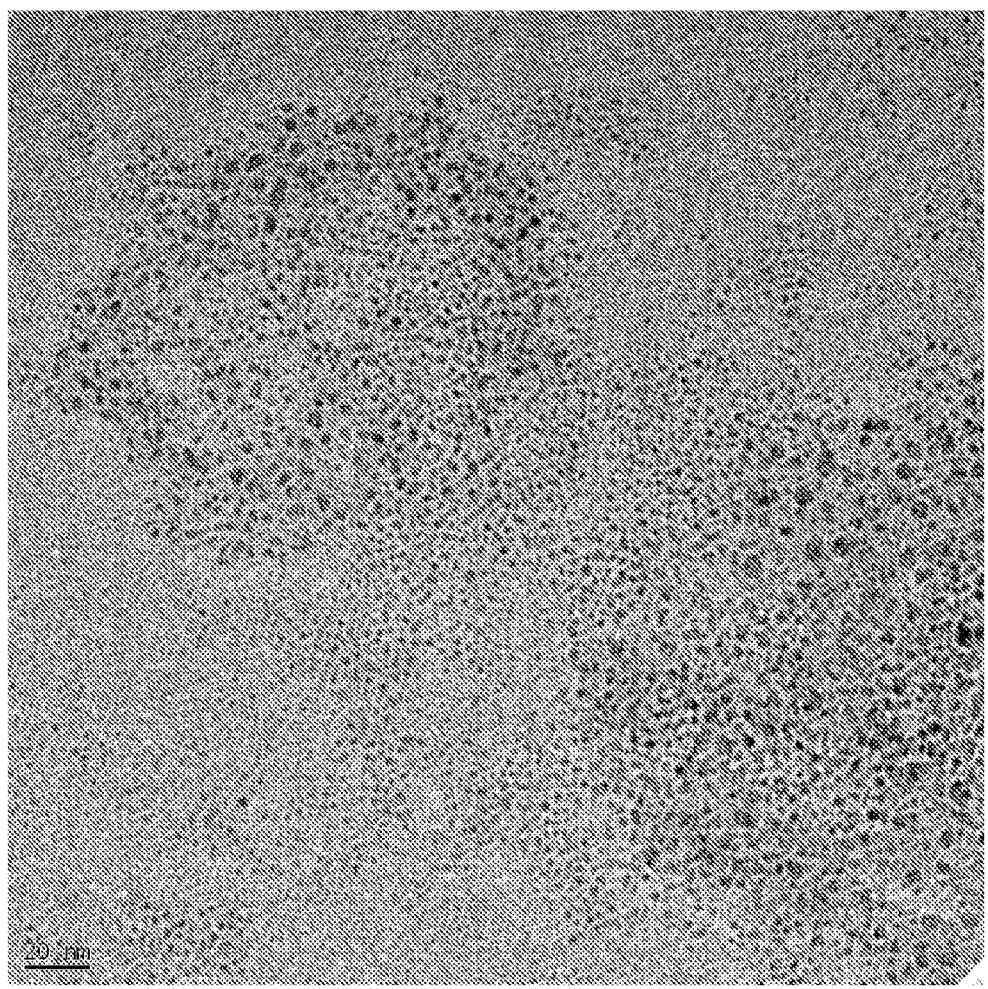
FIG. 2d is a TEM image of particles prepared according to the method of Example 3 showing a particle size distribution of +/−10 nm.
Figure 2E:
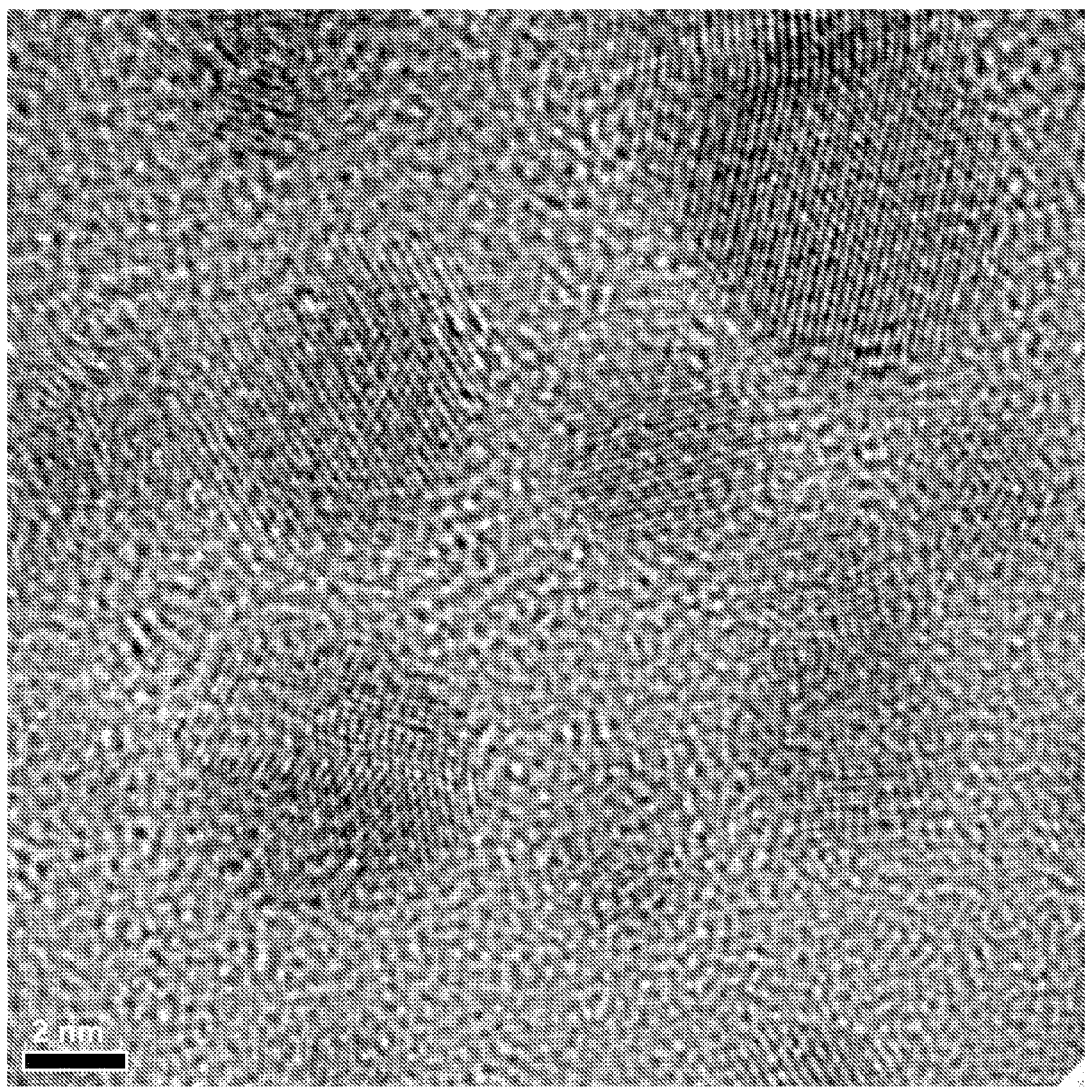
FIG. 2e is a high resolution transmission electron microscopy (HRTEM) image of particles prepared according to the method of Example 3.

The present invention is related to methods for preparing nanoscale HAp particles and the HAp particles prepared therewith. Kits for use in preparing the particles and colloids containing the particles are also presented.

Hydroxyapatite has reported uses for biomedical, chromatographic, and piezoelectric applications and has been synthesized by various techniques. However, reaction conditions for the preparation of HAp such as high temperatures, high pressures and extreme pH values, as well as low yield, vigorous washing requirements, and long reaction times limit biological applications.

The methods of the present invention permit the formation under mild reaction conditions of HAp under conditions suitable for the above uses, especially biological use.

The method involves combining an amount of a calcium ion source, which includes calcium acetate, and an amount of a phosphate ion source, wherein the amounts are sufficient to produce nanoscale HAp particles and the amounts are combined under essentially ambient conditions to produce the HAp particles.

Suitable phosphate ion sources include, but are not limited to, one or more of potassium or sodium orthophosphate; orthophosphoric acid; Group I phosphates, preferably monobasic, dibasic, or tribasic potassium or sodium phosphate; magnesium phosphate; ammonium phosphate; and the like. Potassium or sodium orthophosphate is preferred. In addition to calcium acetate, the calcium ion source may include one or more of calcium hydroxide, calcium oxalate, calcium acetate, calcium nitrate, calcium phosphate, calcium carbonate, calcium fluoride, and calcium chloride. Calcium acetate alone is preferred.

The calcium ion source, the phosphate ion source, or both are in solution prior to combining the sources. Preferably, the solution contains one or more of water, buffer, solvent, simulated body fluid, or fortified cell medium with or without serum. Suitable buffers include, but are not limited to, N-(2-hydroxyethyl)-piperazine-N'-2-ethanesulfonic acid (HEPES), 2-(bis(2-hydroxyethyl)amino)-2-(hydroxymethyl)propane-1,3-diol (BIS-TRIS), 3-(N-Morpholino)-propanesulfonic acid (MOPS), N-(2-Acetamido)-2-aminoethanesulfonic acid (ACES), N-(2-Acetamido)iminodiacetic Acid (ADA), N,N-Bis(2-hydroxyethyl)-2-aminoethanesulfonic Acid (BES), 3-[N,N-bis(2-hydroxyethyl)amino]-2-hydroxypropanesulfonic acid (DIPSO), 4-(N-morpholino)butanesulfonic acid (MOBS), 3-[N-morpholino]-2-hydroxypropanesulfonic acid (MOPSO), piperazine-1,4-bis (2-ethanesulfonic acid) (PIPES), 3-[N-Tris(hydroxymethyl)methylamino]-2-hydroxypropanesulfonic acid (TAPSO), N-Tris(hydroxymethyl)methyl-2-aminoethanesulfonic acid (TES), and acetic acid. A preferred buffer is acetic acid.

If a particular ion source is not in solution, the source is in a solid phase.

An optional step includes agitating the combination until HAp is formed. Agitating the combination accelerates the formation of hydroxyapatite. As used herein, the term "agitate" refers to mechanical movement, for example, vibrating, vortexing, swirling, shaking, ultrasonicating, stirring, or the like that causes mixing. Mechanical movements include movements performed by hand.

When the precursor composition is completely mixed, an extremely viscous gel is formed. This thixotropic material exhibits shear thinning after further intense agitation and returns to a milky solution. Optionally, this solution is allowed to age for a period between 2 minutes and 10 days. During the aging process, additional agitation may or may not be applied to continue mixing. The aging time allows Ostwald ripening of the particles, therefore, the particles aged longer exhibit a larger particle size.

Essentially ambient conditions are employed. A preferred temperature range is between −10° C. and 45° C. At room temperature, HAp particles are typically produced within 1 minute to an hour. Combining the sources while heating will speed up the rate of reaction to more quickly produce HAp, while combining the ion sources while cooling will decrease the rate at which HAp particles form.

During the course of the reaction, a pH swing may occur, which is varied with the calcium to phosphate stoichiometry. A preferred embodiment, in which the calcium to phosphate ratio is about 1.67, exhibits a pH swing of 12 down to 7 over the time of a 4 hour reaction. The pH of the gel phase is 12; just after the shear thinning and return to solution, the pH is 10; after 3 hours of reaction, the pH is 8; and after 4 hours of reaction, the pH returns to neutral. The time to neutral, however, also depends on the employment or omission of agitation throughout the reaction that may enhance kinetics and diffusion of the ions in the formation of hydroxyapatite.

The employment of a buffer as the reaction medium moderates the pH change, which affects the product formed. Hydroxyapatite is formed, but secondary phases of calcium phosphate and calcium carbonate may be additionally formed, but can be remedied through process variations, for example, bubbling with nitrogen, addition of chelating agents, or use of additional pH adjustments or buffers.

Another optional step includes adding one or more dopant ions suitable for substitution into the HAp lattice. Such ions are readily determinable by one of skill in the art. Suitable ions include, but are not limited to, magnesium, fluorine, chlorine, potassium, iron, carbonate, sodium, and the like. The HAp particles of the present invention can also be doped with ions of one or more rare earth elements.

Following the aging process, a washing step can be performed. This step includes, for example, filtration, centrifuging, and/or liquid replacement. Centrifuging or liquid replacement are preferred. Minimal washing cycles are needed because of the non-toxic nature of the ions left in solution. In one embodiment, the citrate wash disclosed in U.S. Pat. No. 6,921,544, the contents of which are incorporated herein by reference in their entirety, is used to remove at least a portion of an amorphous phase if the amorphous phase is considered an undesired impurity.

To produce solid hydroxyapatite, the solution is dried. Suitable drying techniques are readily determinable by those of skill in the art. Preferred drying techniques include evaporative and sublimation-based drying methods, for example, oven drying and freeze drying.

The methods according to the present invention can take place in any suitable reaction system. An exemplary system includes a flow reactor for continuous production of hydroxyapatite.

Powdered HAp particles produced according to the methods of the present invention are also presented. The HAp particles have a BET surface area between about 200 and about 3000 $m^2/g$ and a particle size between about 1 nm and about 9 nm. In one embodiment, the particles have a dispersed particle size between about 1 and about 9 nm. The term "dispersed" is defined herein in the context of colloidal chemistry where the particles maintain an inter-particle spacing such that no physical contact is made between the particles. The term "aggregated" is defined herein as adjacent particles having no inter-particle spacing and making contact with the nearest neighboring particles. In another embodiment, the particles are aggregated and have an aggregated particle size equal to or greater than about 2 nm, preferably between about 2 nm and about 5 mm.

Figure 3A:
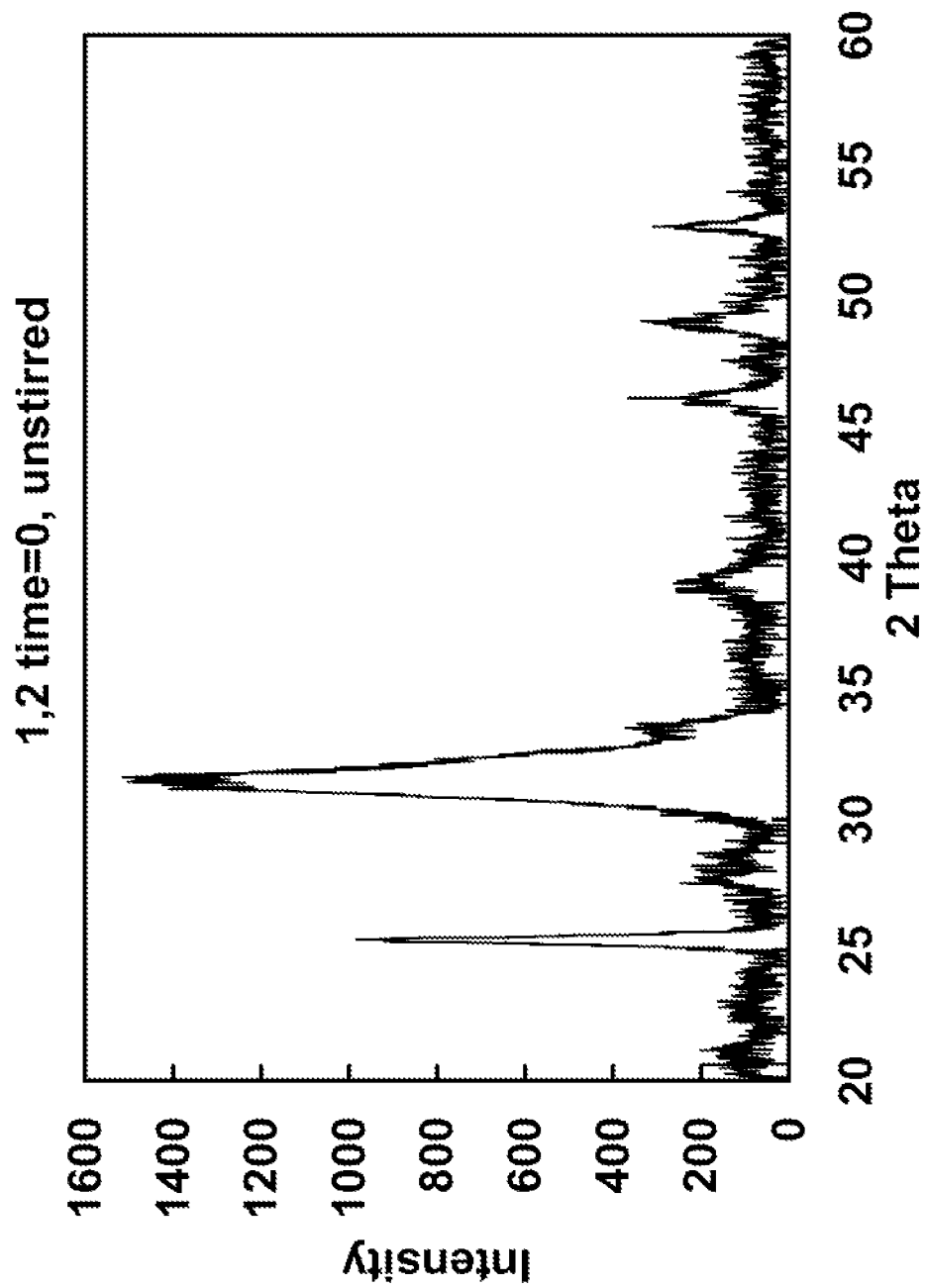
FIG. 3a is an XRD spectrum corresponding to HAp particles prepared according to a method of Example 1.
Figure 3B:
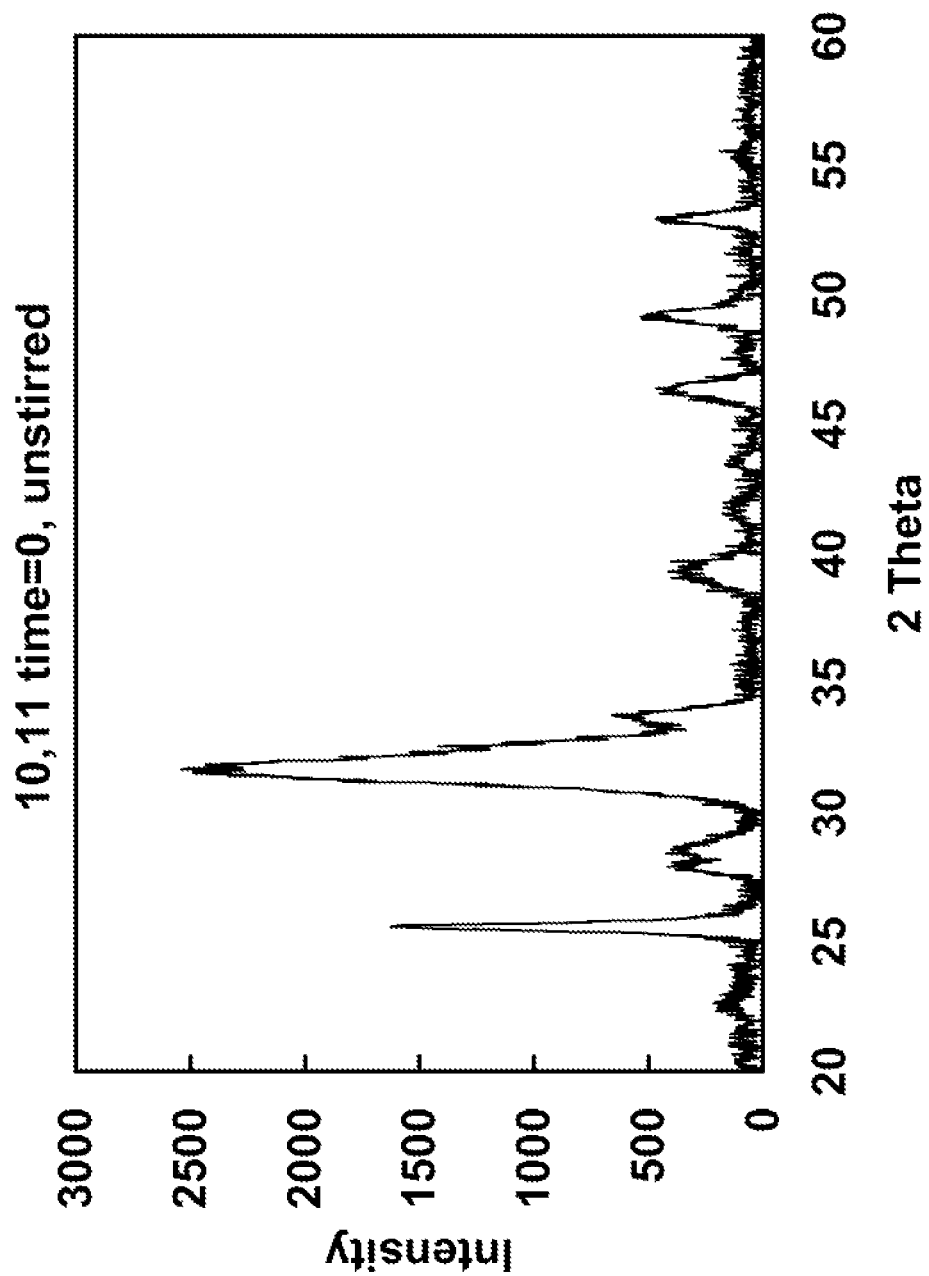
FIG. 3b is an XRD spectrum corresponding to HAp particles prepared according to the method of Example 2.

The composition of the powdered HAp particles is stoichiometric or non-stoichiometric with respect to calcium and phosphate. For example, the XRD diffraction pattern of FIG. 3d represents the results of a standard test for stoichiometry. FIG. 3d shows the presence of peaks corresponding to tricalcium phosphate (TCP) after the sample was heat treated at 900° C. for 2 hours. The presence of TCP indicates a non-stoichiometric composition and/or an amorphous phase. In one embodiment, at least a portion of the composition includes an amorphous phase. In one embodiment, the ratio of calcium to phosphate in the HAp particles is between 1.25 and 2.5.

The HAp particles exhibit a spherical or non-spherical morphology. The term "spherical" is used herein to mean equiaxed particles having either a primary or secondary particle structure.

Given that hydroxyapatite has no toxicity and its components are low cost, such a technology presents great promise for a range of applications.

HAp particles having the size distribution of the present invention are effective in drug delivery because they are more capable of penetrating the cellular wall and carry a much higher surface area for adsorption of drug molecules. The range also allows the particles to be used intravenously as a drug therapy or for transdermal drug delivery. The size range is also important in biomaterial applications because it is close to what is seen naturally in the body. Being smaller, it will also be more readily processable by cells and tissues for regeneration and resorption.

Devices based on hydroxyapatite are typically in the form of polycrystalline ceramics, polymer-ceramic composites, or films on a metallic surface such as titanium. The powders produced in this invention can be used in conventional processes to make all three forms of materials, using conventional methods such as solid state sintering for polycrystalline ceramics, polymer-melt processing for polymer-ceramic composites and plasma spraying for hydroxyapatite-coated titanium metal. The particles of this invention can be grown directly onto the metal surfaces without the need for any high temperature processing.

The hydroxyapatite of the present invention is also useful in the preparation of compounds for use as granular fill for direct incorporation into the hard tissues of humans or other animals, and as bone implantable materials. The present invention thus includes granular fill compounds, bone implant materials, tooth filling compounds, bone cements and dentifrices containing the hydroxyapatite of the present invention. The products are formulated and prepared by substituting the hydroxyapatite of the present invention for hydroxyapatite in conventional hydroxyapatite-based products. The compounds may be prepared from metallic and polymeric hydroxyapatite composites.

Suitable polymers include polysaccharides, poly(alkylene oxides), polyarylates, for example those disclosed in U.S. Pat. No. 5,216,115, block co-polymers of poly(alkylene oxides) with polycarbonates and polyarylates, for example those disclosed in U.S. Pat. No. 5,658,995, polycarbonates and polyarylates, for example those disclosed in U.S. Pat. No. 5,670,602, free acid polycarbonates and polyarylates, for example those disclosed in U.S. Pat. No. 6,120,491, polyamide carbonates and polyester amides of hydroxy acids, for example those disclosed in U.S. Pat. No. 6,284,862, polymers of L-tyrosine derived diphenol compounds, including polythiocarbonates and polyethers, for example those disclosed in U.S. Pat. No. RE37,795, strictly alternating poly(alkylene oxide) ethers, for example those disclosed in U.S. Pat. No. 6,602,497, polymers listed on the United States FDA "EAFUS" list, including polyacrylamide, polyacrylamide resin, modified poly(acrylic acid-cohypophosphite), sodium salt polyacrylic acid, sodium salt poly(alkyl(C16-22) acrylate), polydextrose, poly(divinylbenzene-co-ethylstyrene), poly(divinylbenzene-co-trimethyl(vinylbenzyl)ammonium chloride), polyethylene (m.w. 2.00-21,000), polyethylene glycol, polyethylene glycol (400) dioleate, polyethylene (oxidized), polyethyleneimine reaction product with 1,2-dichloroethane, polyglycerol esters of fatty acids, polyglyceryl phthalate ester of coconut oil fatty acids, polyisobutylene (min. m.w. 37,000), polylimonene, polymaleic acid, polymaleic acid, sodium salt, poly (maleic anhydride), sodium salt, polyoxyethylene dioleate, polyoxyethylene (600) dioleate, polyoxyethylene (600) mono-rici noleate, polyoxyethylene 40 monostearate, polypropylene glycol (m.w. 1,200-3,000), polysorbate 20, polysorbate 60, polysorbate 65, polysorbate 80, polystyrene, cross-linked, chloromethylated, then aminated with trimethylamine, dimethylamine, diethylenetriamine, or triethanolamine, polyvinyl acetate, polyvinyl alcohol, polyvinyl polypyrrolidone, and polyvinylpyrrolidone, and polymers listed in U.S. Pat. No. 7,112,417, the disclosures of all of which are incorporated herein by reference in their entirety.

Also presented is a kit for use in preparing nanoscale HAp particles of the present invention. The kit includes (a) an amount of a calcium ion source comprising calcium acetate and (b) an amount of a phosphate ion source, wherein the amounts are sufficient to produce nanoscale HAp particles when combined under ambient conditions. The kit can be used to prepare HAp particles prior to the introduction of the particles into a patient. Alternatively, the kit can be used to combine components (a) and (b) in a patient in need thereof for the preparation, and subsequent deposit, of HAp particles in vivo. The two ion sources are provided in separate containers. Other components may be present depending upon the intended therapeutic use.

Yet another aspect of the present invention includes a stable colloidal suspension with nanoscale HAp particles suspended in a biocompatible ionic solution prepared according to the methods of the present invention, wherein the ionic solution includes physiological concentrations of phosphate and acetate anions and sodium or potassium cations. Also presented is a stable colloidal suspension with the HAp particles of the present invention suspended in a biocompatible ionic solution.

A suitable ionic solution is readily determinable by one of skill in the art. In one embodiment, the ionic solution includes the mother liquor from which the hydroxyapatite particles were produced. The mother liquor can be formulated to produce an ionic buffer upon HAp formation. For example, the mother liquor could form a phosphate buffered saline (PBS) solution upon formation of HAp. In another embodiment, the ionic solution includes a solution prepared independently of the hydroxyapatite particles, for example, one of the aforementioned buffers.

The following non-limiting examples set forth herein below illustrate certain aspects of the invention.

EXAMPLES

Example 1

Room Temperature Crystallization of Hydroxyapatite in Water

Calcium acetate hydrate (99% Acros Organics, Belgium, CAS #114460-21-8) and potassium orthophosphate hydrate (Acros Organics, Belgium, CAS #27176-10-9) were used as reactants for the synthesis of hydroxyapatite. First, a 1.0 molal calcium acetate hydrate solution was made using distilled, deionized water. Then, a 0.6 molal solution of potassium orthophosphate hydrate was made using distilled, deionized water. Equal volumes of each were then measured out for the reaction to create a calcium to phosphate ratio of 1.67 (final concentrations of ions if they were to remain in solution would be 0.5 m/0.3 m). A 100 mL reaction required 50 mL of the calcium solution to be measured and poured into a beaker and 50 mL of the phosphate solution to be added. Agitation via vortexing was then performed until and through the gelation stage. Once the gel returned to solution, the slurry was then allowed to age for 2 minutes. The concentrate was then dried in an oven at 70° C. for 24 hours and desiccated until use or immediately atomized onto a Transmission Electron Microscopy (TEM) grid for characterization.

X-Ray diffraction (XRD) confirmed the phase formed was hydroxyapatite with no detectable secondary phases or peaks present. FIG. 3a is an XRD diffraction pattern corresponding the HAp particles prepared according to this method, which were washed followed by drying in a 70° C. oven. The broadness of the peaks in FIG. 3a indicates nanoscale particles. Furthermore, the peaks match the standard reference peaks for hydroxyapatite. Helium pycnometry confirms an average particulate density of 2.4 g/cm$^3$.

Figure 3C:
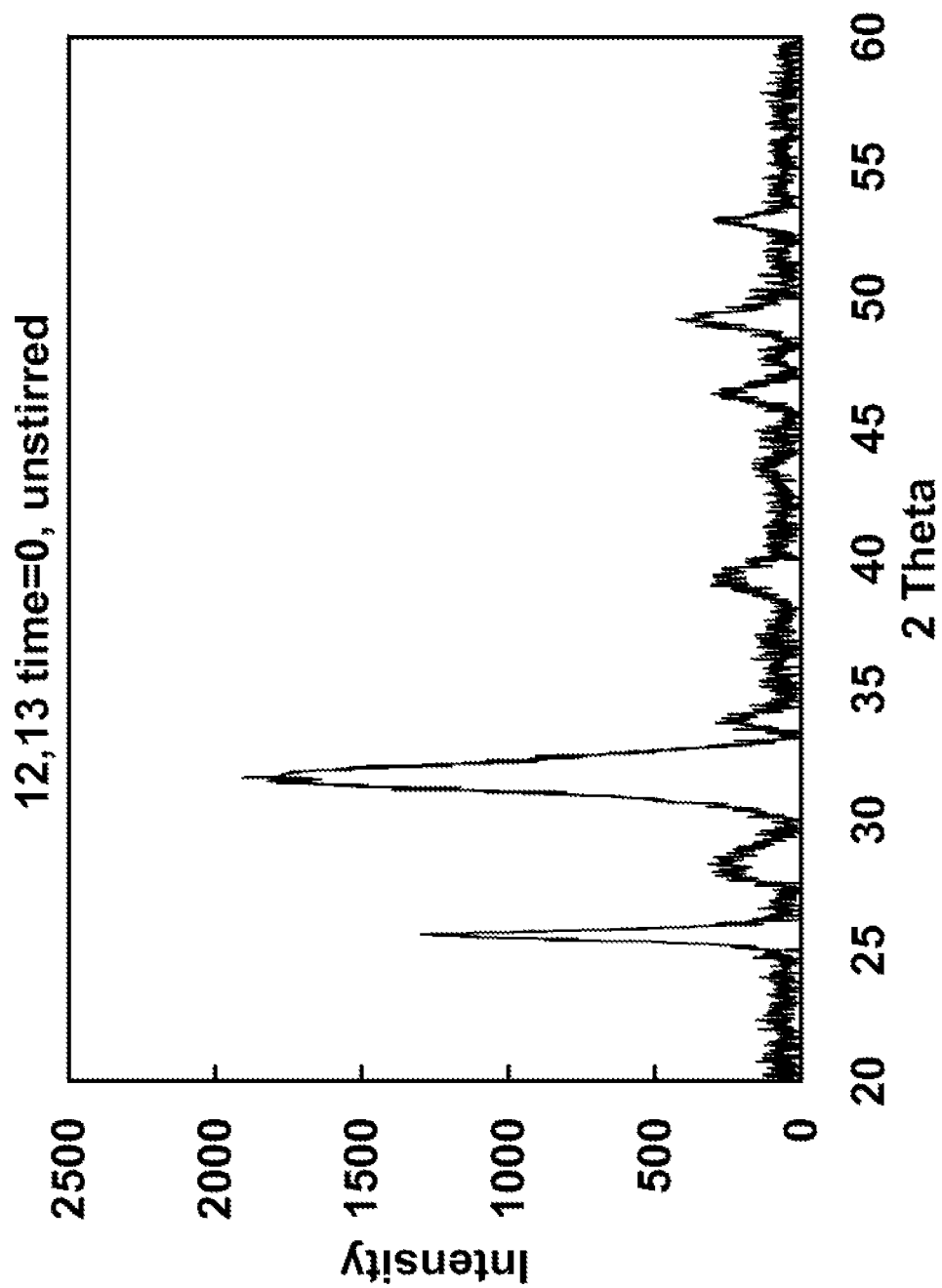
FIG. 3c is an XRD spectrum corresponding to HAp particles prepared according to a method of Example 1, wherein the reactant concentrations were halved.
Figure 3D:
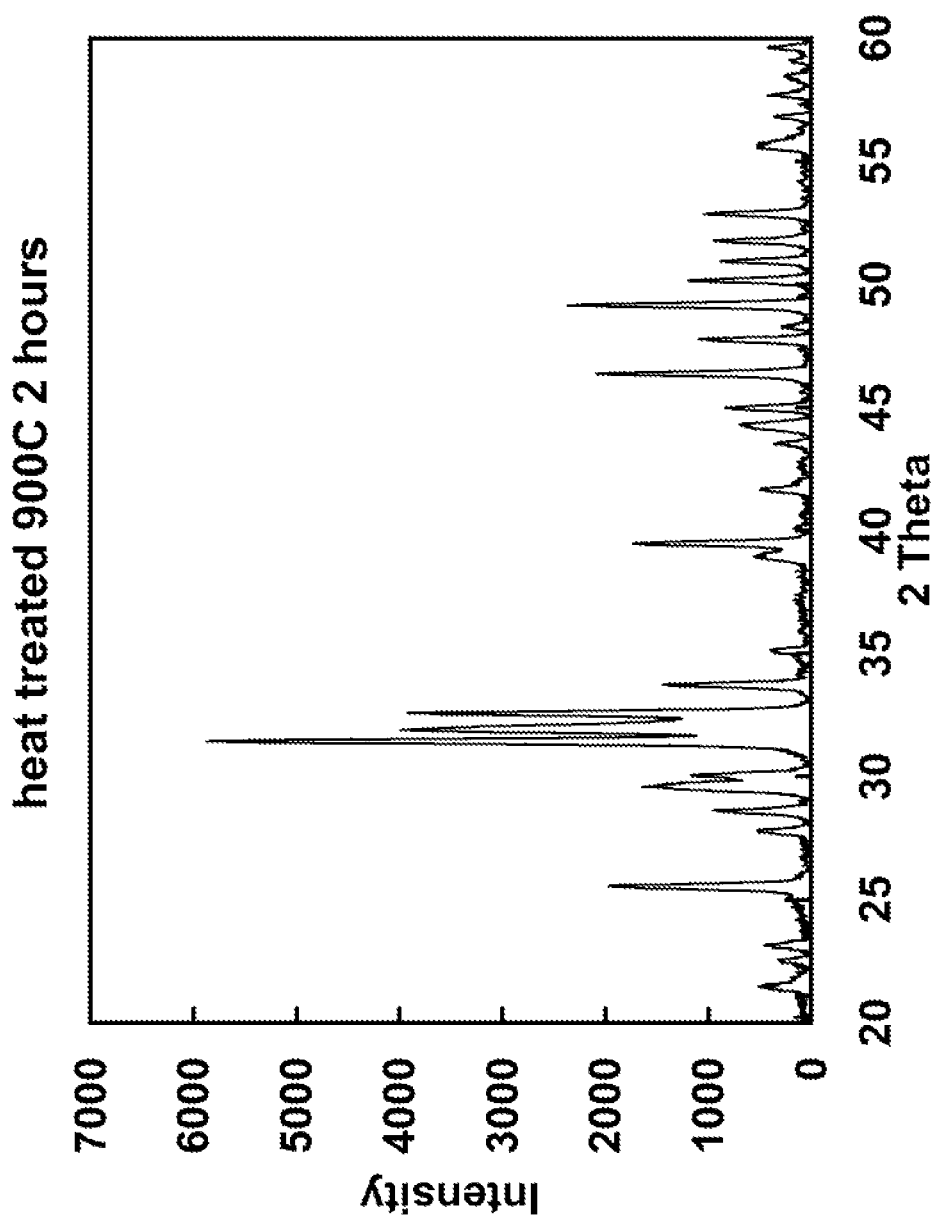
FIG. 3d is an XRD spectrum corresponding to HAp particles prepared according to a method of Example 1, wherein the particles were heat treated at 900° C. for 2 hours.

FIG. 3c is an XRD diffraction pattern corresponding to HAp particles prepared according to this method, wherein the reactant concentrations were halved. FIG. 3c also confirms the presence of HAp particles.

Example 2

Room Temperature Crystallization of Hydroxyapatite in Water

Hydroxyapatite was prepared according to the method of Example 1. However, a 2.0 molal calcium acetate hydrate solution and a 1.2 molal solution of potassium orthophosphate hydrate were used. The final concentrations of ions if they were to remain in solution after mixing would be 1.0 m/0.6 m.

TEM images of the resulting hydroxyapatite particles are shown in FIGS. 1a-d. These images show lattice fringes indicating crystallinity of the particles and also show relatively uniform particle size and morphology.

The XRD diffraction pattern is shown in FIG. 3b, which also confirms the presence of HAp particles.

Example 3

Room Temperature Crystallization of Hydroxyapatite in a Self Buffering Solution

Calcium acetate hydrate and potassium orthophosphate hydrate solutions were prepared as described in Example 1. The potassium orthophosphate hydrate solution was divided in half and acetic acid was added to one of the two portions until the pH of the solution was 7.4 (volume depends on total solution volume, for example 500 mL solution needs about 23 mL of glacial acetic acid). Proportional amounts of each of the three solutions were then measured out to create a calcium to phosphate ratio of 1.67 and pH of 7.4 (final concentrations of ions if they were to remain in solution would be 0.5 m/0.3 m). A 20 mL reaction required 10 mL of the calcium solution to be measured and poured into a beaker and 8.5 mL of the phosphate solution (unadjusted) to be added to the calcium solution followed by 1.5 mL of the pH adjusted solution. Agitation via stirring with a glass rod was then performed until the solution appeared completely mixed and white (a gelation is not seen). The slurry was not aged. The concentrate or solution was then dried in an oven at 70° C. for 24 hours and desiccated until use or immediately atomized onto a TEM grid for characterization.

X-Ray diffraction confirmed the phase formed was hydroxyapatite with no detectable secondary phases or peaks present. An average density of 2.2 g/cm$^3$ was determined via Helium pycnometry.

TEM images of the resulting hydroxyapatite particles are shown in FIGS. 2a-e. These images show lattice fringes indicating crystallinity of the particles and also show relatively uniform particle size and morphology. Dispersed particles having a particle size less than 10 nm are shown.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A composite material comprising hydroxyapatite particles and a polymer, wherein the particles have a BET surface area between about 200 and about 3000 m$^2$/g and a particle size wherein the largest dimension of any particle is between about 1 nm and about 9 nm, said articles comprising crystals with a dominant lattice spacing of about 0.28 nm.

2. The material of claim 1, wherein the hydroxyapatite particle has a dispersed particle size between about 1 and 9 nm.

3. The material of claim 1, wherein the hydroxyapatite particle has an aggregated particle size between about 2 in and 5 nm.

4. The material of claim 1, wherein the hydroxyapatite is stoichiometric or non-stoichiometric with respect to calcium and phosphate.

5. The material of claim 1, wherein the hydroxyapatite includes an amorphous phase.

6. The material of claim 1, wherein the ratio of calcium to phosphate of the hydroxyapatite is between 1.25 and 2.5.

7. The material of claim 1, further comprising one or more dopant ions.

8. The material of claim 3, wherein the polymer comprises a polysaccharide, poly(alkylene oxide), polyarylate, block co-polymer of poly(alkylene oxide) with polycarbonate and polyarylate, polycarbonate, polyarylate, free acid polycarbonate and polyarylate, polyamide carbonate and polyester amide of hydroxy acid, L-tyrosine derived diphenol compound, including polythiocarbonate and polyether, strictly alternating poly(alkylene oxide) ether, polyacrylamide, polyacrylamide resin, modified poly(acrylic acid-cohypophosphite), sodium salt polyacrylic acid, sodium salt poly(alkyl (CI6-22) acrylate), polydextrose, poly(divinylbenzene-co-ethylstyrene), poly(divinylbenzene-co-trimethyl (vinylbenzyl)ammonium chloride), polyethylene (m.w. 2.00-21,000), polyethylene glycol, polyethylene glycol (400) dioleate, polyethylene (oxidized), polyethyleneimine reaction product with 1,2-dichloroethane, polyglycerol esters of fatty acid, polyglyceryl phthalate ester of coconut oil fatty acid, polyisobutylene (min. m.w. 37,000), polylimonene, polymaleic acid, polymaleic acid, sodium salt, poly(maleic anhydride), sodium salt, polyoxyethylene dioleate, polyoxyethylene (600) dioleate, polyoxyethylene (600) mono-rieinoleate, polyoxyethylene 40 monostearate, polypropylene glycol (m.w. 1,200-3,000), polysorbate 20, polysorbate 60, polysorbate 65, polysorbate 80, polystyrene, cross-linked, chloromethylated, then aminated with trimethylamine, dimethylamine, diethylenetriamine, or triethanolamine, polyvinyl acetate, polyvinyl alcohol, polyvinyl polypyrrolidone, and polyvinylpyrrolidone.

9. A stable colloidal suspension comprising the material of claim 3 suspended in a biocompatible ionic solution.

10. The material of claim 1 further comprising a drug.

* * * * *